(12) United States Patent
Markwort et al.

(10) Patent No.: US 9,182,357 B2
(45) Date of Patent: Nov. 10, 2015

(54) SEMICONDUCTOR WAFER INSPECTION SYSTEM AND METHOD (75) Inventors: Lars Markwort, Haimhausen (DE); Ernst Hegels, Kirchheim b. München (DE)

(73) Assignee: Nanda Technologies GmbH, Unterschleissheim (DE)

( * ) Notice: Subject to any disclaimer, the term of this patent is extended or adjusted under 35 U.S.C. 154(b) by 808 days.

(21) Appl. No.: 13/518,349

(22) PCT Filed: Dec. 23, 2010

(86) PCT No.: PCT/EP2010/007925
§ 371 (c)(1),
(2), (4) Date: Jun. 21, 2012

(87) PCT Pub. No.: WO2011/076429
PCT Pub. Date: Jun. 30, 2011

(65) Prior Publication Data
US 2012/0268585 A1    Oct. 25, 2012

(30) Foreign Application Priority Data
Dec. 23, 2009   (EP) ..................... 09015996

(51) Int. Cl.
*H04N 7/18*       (2006.01)
*G01N 21/95*      (2006.01)
*H01L 21/68*      (2006.01)
*H01L 23/544*     (2006.01)

(52) U.S. Cl.
CPC .......... *G01N 21/9501* (2013.01); *H01L 21/681* (2013.01); *G01N 21/9503* (2013.01); *H01L 23/544* (2013.01); *H01L 2223/54493* (2013.01)

(58) Field of Classification Search
CPC .......... G01N 21/9501; G01N 21/9503; H01L 2223/54493; H01L 23/544
See application file for complete search history.

(56) References Cited

U.S. PATENT DOCUMENTS

| | | | |
|---|---|---|---|
| 8,204,298 B2 * | 6/2012 | Vaughnn ...................... | 382/151 |
| 2002/0071129 A1 | 6/2002 | Chen et al. | |
| 2003/0085368 A1 | 5/2003 | Kesil et al. | |
| 2003/0133133 A1 | 7/2003 | Fujiwara et al. | |

(Continued)

FOREIGN PATENT DOCUMENTS

| | | |
|---|---|---|
| DE | 102 54 542 A1 | 1/2004 |
| TW | 200827709 A | 7/2008 |

(Continued)

OTHER PUBLICATIONS

European Search Report mailed on May 21, 2010 for EP Application No. EP 09 01 5996.3 filed on Dec. 23, 2009, 2 pages.

(Continued)

*Primary Examiner* — Andy Rao
*Assistant Examiner* — Tyler Edwards
(74) *Attorney, Agent, or Firm* — Silicon Valley Patent Group LLP (57) ABSTRACT

A wafer inspection system comprises a camera having a field of view, an object mount configured to position at least a portion of surface 5 of an object 3 at an object plane 15 relative to the camera and within the field of view of the camera and at least one surface portion 41 carrying a multitude of retroreflectors 95 disposed at a greater Δd distance from the camera than the object plane and within the field of view of the camera.

22 Claims, 8 Drawing Sheets

(56) References Cited

U.S. PATENT DOCUMENTS

2007/0058168 A1     3/2007    Michael et al.
2008/0144014 A1     6/2008    Vollrath et al.

FOREIGN PATENT DOCUMENTS

WO    WO 2006/048857 A1    5/2006
WO    WO 2009/121628 A2    10/2009

OTHER PUBLICATIONS

International Search Report and Written Opinion mailed on Apr. 20, 2011 for PCT Application No. PCT/EP2010/007925 filed on Dec. 23, 2010, 7 pages.

Machine Translation in English of Abstract of DE 102 54 542 filed on Jan. 22, 2004 visited at www.espacenet.com on Mar. 13, 2013, 1 page.

\* cited by examiner

SEMICONDUCTOR WAFER INSPECTION SYSTEM AND METHOD

CROSS-REFERENCE TO RELATED APPLICATIONS

This application is the National Stage of International Patent Application No. PCT/EP2010/007925, filed Dec. 23, 2010, which, in turn, claims the benefit of European Patent Application No. 09 015 996.3, filed Dec. 23, 2009, both of which are incorporated herein by reference in their entirety.

BACKGROUND OF THE INVENTION

1. Field of the Invention

The present invention relates to semiconductor wafer inspection systems and semiconductor wafer inspection methods.

2. Brief Description of Related Art

Semiconductor circuits are manufactured by forming micro-patterned structures on a flat semiconductor wafer substrate using lithographic methods. A wafer substrate may have a diameter of about 300 mm, wherein several hundred circuits are arranged in individual dies typically having diameters in the order of some millimeters to some 10 mm, wherein the structures of the semiconductor circuits may have dimensions below 0.1 μm. It is desirable to detect defects in the manufactured patterns and deficiencies of a manufacturing process at early stages of the semiconductor manufacture.

Several techniques are known for inspection of semiconductor substrates. These techniques try to locate defects on a wafer substrate in a coordinate system defined relative to the wafer substrate. The coordinate system of the wafer may be defined such that it has its origin in a center of the wafer, wherein an orientation of the coordinate system is defined relative to a wafer notch.

In a process of semiconductor wafer inspection it is necessary to map coordinates of defects as detected in a coordinate system of an inspection tool to the coordinate system of the wafer. Conventional inspection methods involve special tools and methods for detecting a wafer edge to finally determine the center of a particular wafer on the inspection, and to detect the wafer notch to determine the orientation of the wafer.

The tools and methods for wafer edge and notch detection have sometimes been found to be insufficient and complicated.

SUMMARY OF THE INVENTION

The present invention has been accomplished taking the above problems into consideration.

It is an object of the present invention to provide systems and methods allowing to detect a position of an object relative to a reference.

Embodiments of the present invention provide detection systems and methods allowing to determine a position of an object relative to a reference. Particular embodiments of the present invention provide inspection systems and methods allowing to accurately position objects relative to a reference, such as a coordinate system of an inspection tool. Further particular embodiments of the invention provide systems and methods for inspecting objects, such as semiconductor wafers, and to map detected defects and deficiencies to a coordinate system of the object.

According to embodiments, a detection system comprises a camera, object mount configured to hold an object at a distance from the camera, and at least one surface portion carrying a multitude of retroreflectors, wherein the surface portion is disposed farther away from the camera such that the object overlaps, when seen from the camera, with the surface portion carrying the multitude of retroreflectors.

It has been found that an edge or outline of the object can be detected with a high accuracy based on an image recorded by the camera, if a retroreflecting surface or retroreflecting surface portion are positioned behind the edge or outline of the object. Compared to conventional arrangements, where surfaces reflecting light according to Lambert's law are positioned behind an object, the retroreflecting surface allows a determination of the edge or outline of the object from the recorded image with a higher accuracy.

According to embodiments herein, the retroreflecting surface which has a multitude of retroreflectors on it has an optical property such that, when a collimated beam of light is incident on the surface portion under an incidence angle of 2° relative to a surface normal, an angular intensity distribution of light reflected from the surface is formed such that a maximum intensity of reflected light is directed away from a location of incidence of the collimated beam on the surface under an angle of more than 1° relative to the surface normal. In particular embodiments, the direction of the maximum intensity of light reflected from the surface has an angle relative to the surface normal which is close to or the same as the angle of incidence of the incident light relative to the surface normal. This may also hold if the angle of incidence is 5°, 10° or greater. According to other particular embodiments, the angle between the surface normal and the direction of the maximum intensity of the reflected light is greater than one half of the angle of incidence of the incident light relative to the surface normal. Further, the following property can be fulfilled: an angle between a direction of incidence of a light beam and a direction of the maximum intensity of the reflected light is smaller than an angle between the direction of incidence of the light beam and a surface normal of the surface portion.

According the exemplary embodiments, a detection system comprises a camera having a field of view, an object mount configured to position at least a surface portion of an object at an object plane relative to the camera and within the field of view of the camera, and at least one surface portion carrying a multitude of retroreflectors disposed at a greater distance from the camera than the object plane and within the field of view of the camera.

According to particular embodiments herein, a difference in distance from the camera between the at least one surface portion carrying the multitude of retroreflectors and the object plane is greater than 0.3 mm, greater than 2.0 mm, or greater than 7.0 mm.

According to other embodiments, a detection system comprises optics configured to provide an imaging beam path from an object plane onto a light sensitive substrate of a camera. The optics provides a numerical aperture at an object side of the imaging beam path, NA, and is designed to use light within a certain wavelength range for the imaging. The following relation is fulfilled in such embodiment:

$$\Delta d > \frac{1}{20} \frac{2\lambda}{NA^2}$$

wherein λ is one exemplary wavelength out of the wavelength range, and Δd is a distance difference between a distance of the object plane from the camera and a distance of the at least one surface portion from the camera, wherein the surface portion carries a multitude of retroreflectors. According to other embodiments, one or more of the following relations can be fulfilled:

$$\Delta d > 0.5 \lambda/NA^2, \Delta d > 2.0 \lambda/NA^2 \text{ and } \Delta d > 10.0 \lambda/NA^2.$$

According to embodiments, an inspection system comprises optics configured to provide both a bright field illumination beam path from a light source to an object plane and an imaging beam path from the object plane to a camera, wherein an angle at the object plane between a main axis of the imaging beam path and a main axis of the bright field illumination beam path is smaller than 5°, smaller than 2° or even smaller than 1°. Herein, at least one surface portion carrying a multitude of retroreflectors is disposed at a greater distance from the camera than the object plane, wherein the distances are measured along the main axis of the imaging beam path.

According to other embodiments, an inspection system comprises optics configured to provide both an imaging beam path from an object plane to a light sensitive substrate of a camera and a dark field illumination beam path from a light source to the object plane, wherein an angle at the object plane between a main axis of the imaging beam path and a main axis of the dark field illumination beam path is greater than 5°, greater than 10° or even greater than 20°. Herein, at least one surface portion carrying a multitude of retroreflectors is disposed at a greater distance from the camera than the object plane, wherein the distance is measured along the main axis of the imaging beam path.

According of embodiments, a positioning system comprises a detection system as illustrated with respect to one of the embodiments outlined above, an object mount configured to hold an object, and an actuator configured to displace the object mount in a direction transverse to a beam path from the object to a camera and/or to rotate the object about an axis oriented transverse to a plane which is oriented orthogonal to the beam path from the object to the camera.

According to particular embodiments herein, the actuator is controlled by a controller which receives images from the camera and which controls a displacement or rotation of the object, via the actuator, based on an analysis of one or more images recorded by the camera and received by the controller.

According to embodiments, the object which is detected, positioned or inspected according to embodiments of the systems and methods outlined above is a semiconductor wafer, wherein an outline of the wafer including a wafer edge and/or a wafer notch is detected.

According to embodiments, a semiconductor wafer inspection system comprises: optics comprising an objective lens and a beam splitter; a bright-field light source; an image detector having a radiation sensitive substrate; and a wafer support for mounting the semiconductor wafer in the object plane; wherein the optics provides an imaging beam path in which the object plane, the objective lens, the beam splitter and the radiation sensitive substrate are arranged in this order to image a field of view of the object plane onto the substrate of the image detector; wherein the optics provides a bright-field illumination beam path in which the bright-field light source, the beam splitter, the objective lens, and the object plane are arranged in this order to illuminate the field of view with bright-field illumination light; wherein the wafer support comprises at least one first actuator configured to displace the wafer within the field of view relative to the objective lens; and wherein the system further comprises at least one surface portion carrying a multitude of retroreflectors disposed at a greater distance from the objective lens than the object plane and partially overlapping with the semiconductor wafer within the field of view of the camera.

According to an embodiment herein, the surface portion is attached to a component of the wafer support which is displaced by the at least one actuator relative to the objective lens together with the wafer.

This may have an advantage in that an amount of retroreflective material extending beyond the semiconductor wafer is always the same and independent of the position of the wafer within the field of view. Even if the first actuator is operated to displace the wafer, the amount of retroreflective material extending beyond the semiconductor wafer remains unchanged within the field of view and in the image recorded by the image detector. The determining of the position of the wafer within the field of view is mainly based on an analysis of the light reflected from the retroreflecting material. An image feature associated with the retrorefelcting material has, for example, a constant ring shape, independent of the position of the wafer within the recorded image. The only image feature that is changed by moving the wafer within the field of view, is the position of the image feature, for example the constant ring shape. The position of such constant image feature within the recorded image can be determined with a high accuracy. Therefore, it is also possible to determine the true position of the wafer within the field of view with a high accuracy based on the analysis of the recorded image containing the constant image feature at image positions which depend only on the position of the wafer within the field of view.

According to an embodiment herein, the wafer support comprises a movable grip portion and a second actuator configured to push the grip portion against an edge of the semiconductor wafer, and wherein the movable grip portion includes at least one surface portion carrying a multitude of retroreflectors.

The movable grip portion is used to attach and fix the wafer on the wafer support. For example, the wafer support may comprise three grip portion, wherein two grip portion are fixed relative to the wafer support and are configured to be in engagement with the wafer edge, and wherein the third grip portion is configured to move relative to the support and push the wafer edge against the two other grip portions.

The surface portion of retroreflective material on the movable grip portion may have an advantage in that a position of the wafer notch can be determined with a high accuracy also in situations in which the wafer notch happens to rest in a region of the movable grip portion.

According to an embodiment, the optics is configured to have a telecentric property such that an orientation of chief rays of the bright-field illumination beam path varies across the field of view by less than 5° and such that an orientation of chief rays of the imaging beam path varies across the object field by less than 5°.

With such telecentric property a determination of the position of the wafer within the field of view is possible with a relatively high accuracy, even if a distance between the wafer surface or edge and the retroreflective surface portion is relatively large.

According to a further embodiment, the optics is configured such that a numerical aperture of the imaging beam path on a side of the object plane is less than 0.1, and such that a numerical aperture of the bright-field illumination beam path on a side of the object plane is less than 0.1.

With such relatively low numerical aperture, a determination of the position of the wafer within the field of view is possible with a relatively high accuracy, even if a distance between the wafer surface or edge and the retroreflective surface portion is relatively large.

According to embodiments, an embodiment of a semiconductor wafer inspection method comprises: loading a semiconductor wafer into a semiconductor wafer inspection system such that the semiconductor wafer and a multitude of retroreflectors are disposed in a field of view of an imaging system such that the semiconductor wafer shadows a portion of the multitude of retroreflectors; directing, via the imaging optics, bright-field illumination light towards the semiconductor wafer and the multitude of retroreflectors; recording a first image of the semiconductor wafer and the multitude of retroreflectors in the field; analyzing the recorded first image; adjusting a position of the semiconductor wafer relative to the field of view by displacing the semiconductor wafer in a direction transverse to a direction of the bright-field illumination light incident on the semiconductor wafer based on the analysis of the recorded first image and/or rotating semiconductor wafer about an axis oriented transverse to a surface of the wafer based on the analysis of the recorded first image.

According to an exemplary embodiment herein, the method further comprises attaching the multitude of retroreflectors to the semiconductor wafer such that the displacing of the semiconductor wafer includes a displacing of the multitude of retroreflectors together with the semiconductor wafer.

According to a further exemplary embodiment, the analyzing of the recorded first image comprises identifying an edge of the semiconductor wafer in the recorded first image and determining a position of a center of the semiconductor wafer within the field of view based on the identified edge; and identifying a notch of the semiconductor wafer in the recorded first image and determining an orientation of the semiconductor wafer within the field of view based on the identified notch.

According to an exemplary embodiment herein, the adjusting of the position of the semiconductor wafer comprises positioning the semiconductor wafer such that the center of the wafer coincides with a predetermined position and such that the orientation of the wafer coincides with a predetermined orientation.

According to embodiments, the method further comprises loading, one after the other, a plurality of semiconductor wafers into the semiconductor wafer inspection system, wherein the position of each semiconductor wafer is adjusted such that the center of the semiconductor wafer coincides with the predetermined position and such that the orientation of the semiconductor wafer coincides with the predetermined orientation, and wherein the method further comprises recording of a second image of each semiconductor wafer subsequent to the adjusting of the position of the semiconductor wafer, and determining a presence of defects on a given semiconductor wafer based on a comparison of the recorded second image of the given semiconductor wafer with recorded second images of other semiconductor wafers.

With such method each of the plurality of wafers can be precisely and reproducibly positioned relative to the field of view, such that an image analysis including a wafer-to-wafer comparison can be used to detect defects and deficiencies in the individual wafers.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

DETAILED DESCRIPTION OF EXEMPLARY EMBODIMENTS

In the exemplary embodiments described below, components that are alike in function and structure are designated as far as possible by alike reference numerals. Therefore, to understand the features of the individual components of a specific embodiment, the descriptions of other embodiments and of the summary of the invention should be referred to.

Figure 1:
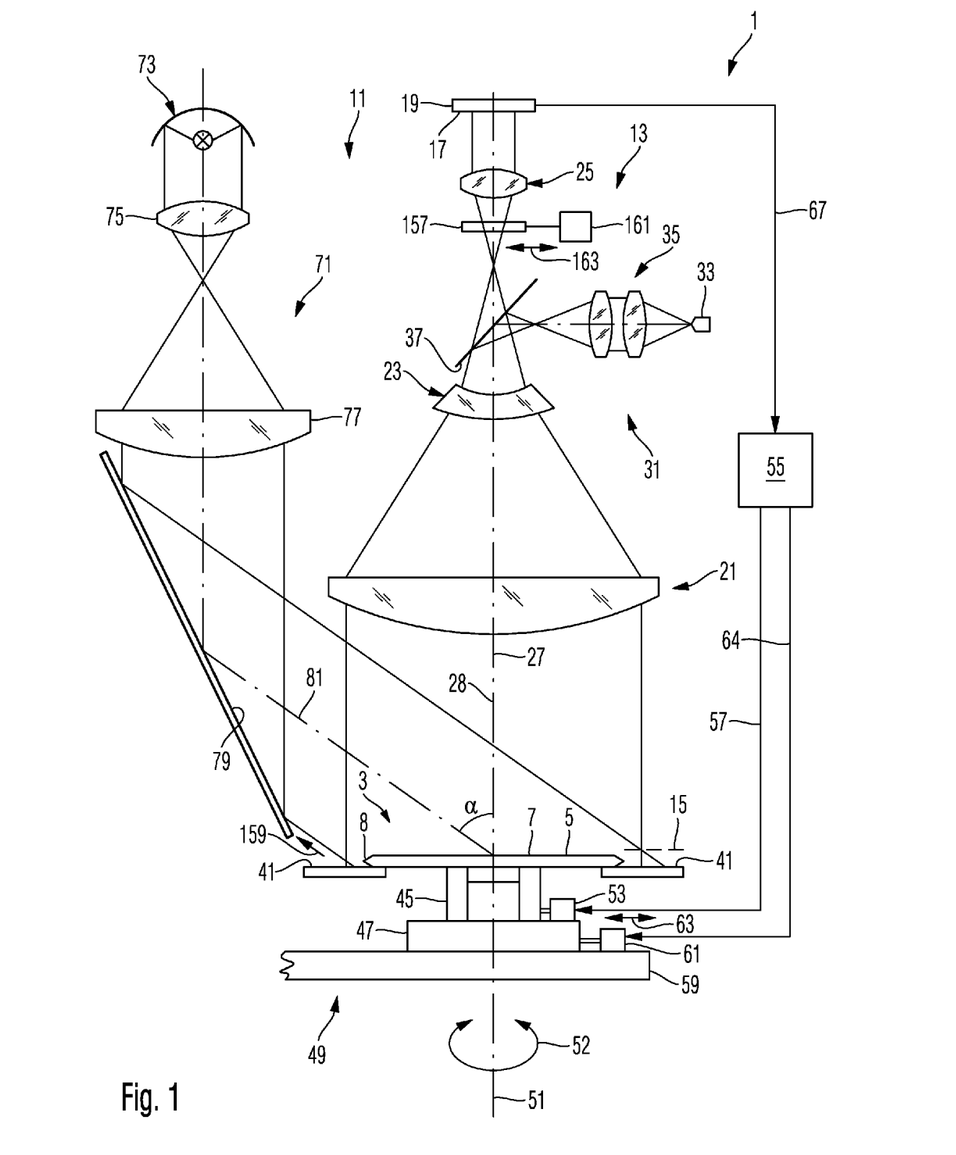
FIG. 1 is a schematic illustration of a semiconductor wafer inspection system.

FIG. 1 is a schematic illustration of a semiconductor wafer inspection system 1 which is configured to detect, position and inspect a semiconductor wafer 3. The semiconductor wafer has a wafer surface 5 provided on a substrate 7. The wafer surface may carry structures manufactured by lithographic processes, and the wafer surface 5 may be covered by layers such as resist layers or protective layers applied to the surface during manufacturing steps of the semi-conductor structures. The system 1 includes optics providing an imaging beam path, a bright-field illumination beam path and a dark-field illumination beam path. The illustration of these beam paths in FIG. 1 and in the following description is simplified and sufficiently detailed as necessary for illustrating the present exemplary embodiment. A more detailed description of suitable optics which can be used in the illustrated example is disclosed in WO 2009/121628 A2, the disclosure of which is incorporated herein by reference.

The optics 11 of the system 1 provides an imaging beam path 13 used for imaging an object plane 15 in which the surface of the wafer 3 can be positioned onto a light sensitive substrate 17 of a detector 19. The imaging beam path 11 is provided by an objective lens 21 which may be composed of one or more lens elements, a lens 23 which can be composed of one or more lens elements, and a lens 25 which can be composed of one or more lens elements. The imaging beam path 11 has a main axis 27 which is, in the present example, oriented orthogonal to the object plane 15.

The optics 11 further provides a bright field illumination beam path 31 from a light source 33 to the object plane 15. The bright field illumination beam path 31 is provided by a lens 35 which can be composed of one or more lens elements, a semi-transparent mirror 37 which is traversed by the imaging beam path 13 and which folds the bright field illumination beam path 31, and the lenses 23 and 21 which are also traversed by the imaging beam path 13. According to other examples, a semitransparent mirror can be traversed by the bright field illumination beam path while the imaging beam path is folded by the semitransparent mirror.

Light emitted by the light source 33 is directed via the bright field illumination beam path 31 towards the object plane 15. The bright field illumination light is incident on the semiconductor wafer 3, and retroreflecting surface portions 41 attached to the wafer 3. The retroreflecting surface portions 41 are configured and positioned such that they are located farther away from the light sensitive substrate 17 of the camera 19 and the light source 13 than the object plane 15, wherein distances between the object plane 15 and the surface portions 41 is measured along the imaging beam path 13 and/or the bright field illumination beam path 31, respectively, i.e. along the direction of the main axis 27 of the imaging beam path or a main axis 28 of the bright field illumination beam path. According to other embodiments, the retroreflecting surface portions 41 can be fixedly attached to the base 59 of the stage 49.

The main axis 28 of the bright field illumination beam path 31 is oriented orthogonal to the object plane 15 in the illustrated example, and it also substantially coincides with the main axis 27 of the imaging beam path 13. According to other examples, a small angle of less than 5°, less than 2°, or less than 1° can be included between the main axes 27, 28 of the imaging beam path 13 and the bright field illumination beam path 31, respectively.

The wafer 3 is supported by a wafer mount 45. The wafer mount 45 may carry the wafer 3 by supporting its back surface, wherein the wafer 3 rests on the wafer mount 45 and is attached thereto due to its own gravity and friction. According to other examples, the wafer mount 45 may include fingers which are attached to an edge 8 of the wafer 3. An example of another wafer mount which could be used in the present example is shown in US 2003/0085368 A1.

The wafer mount 45 is supported by a component 47 of a stage 49, wherein the wafer mount 45 is rotable relative to the component 47 about an axis 51 as indicated by an arrow 52. An actuator 53, such as a motor or a piezoelectric actuator, is provided for controlling a rotary motion of the wafer mount 45 relative to component 47 of the stage 49. The actuator 53 is controlled by a controller 55 via a control line 57.

The component 47 of the stage 49 is supported by a base 59 of the stage 49 wherein the component 47 can be displaced relative to the base 59 in a direction transverse to the main axes 27, 28, of the imaging beam path 13 and bright field illumination beam path 31, respectively. An actuator 61, such as a motor or piezoelectric actuator, is provided to displace the component 47 relative to the base 59 as indicated by an arrow 63. The actuator 61 is controlled by the controller 55 via a control line 64.

The system 1 may comprise a further intermediary component, which is not shown in FIG. 1, between component 47 and base 59 to displace the wafer mount 45 in a further direction transverse to the direction 63 and axis 51 such that the wafer can be displaced in two non-collinear directions transverse to the main axis 27 and 28 and rotated about axis 51 which is transverse to the two directions of displacement. With such arrangement of the stage 59 it is possible to position the wafer 3 carried by the wafer mount 45 as desired relative to the illumination beam path 31 and the imaging beam path 13. The positioning of the wafer 3 is controlled by the actuators 53, 61 which in turn are controlled by the controller 55. The controller 55 generates control signals for the actuators 53, 61 based on images recorded by the camera 19 and transmitted to the controller via a control line 67. The controller 55 analyses the recorded image to detect the wafer edge 8 and/or a wafer notch as illustrated in more detail below. Based on the detected wafer edge and/or wafer notch it is possible to determine, for example, a center of the wafer and an orientation of the wafer relative to a coordinate system of the system 1. It is then possible to determine, for example, a mapping between a coordinate system of the wafer which may be defined relative to its center and notch and the coordinate system of the system 1.

The controller may analyse the image recorded by the camera for defects and deteriorations on the wafer surface 5 and map coordinates of the defects and deteriorations as detected in the coordinate system of the system 1 to the coordinate system of the wafer. The controller may then output coordinates of the defects defected in the coordinate system of the wafer.

The optics 11 further provides a dark field illumination beam path 71 from a dark field illumination light source 73 to the object plane 15, wherein the dark field illumination beam path is provided by a collimating lens 75 which can be composed of one or more lens elements and an objective lens 77 which can be composed of one or more lens elements and a mirror 79. A main axis 81 of the dark field illumination beam path 71 is oriented at the object plane 15 under an angle α relative to the main axis 27 of the imaging beam path 13. The angle α can be greater than 5° or greater than 10° and is about 45° in the illustrated embodiment. Other embodiments may use even larger angles α, such as 60°.

Images of the wafer surface can be recorded by the camera either under bright field illumination if the bright field light source 33 supplies light to the wafer surface, or under dark field illumination if the dark field light source 73 supplies light to the wafer surface. Images recorded under bright field illumination and under dark field illumination provide complementary sources of information about defects and deteriorations located on the wafer and which can be analysed and located by the controller 55 and mapped to the coordinate system of the wafer.

Still further, it possible to adjust the position and orientation of the wafer relative to the system such that the center of each inspected wafer is positioned at a predetermined position relative to the field of view of the optics of the system, and such that the orientation of the wafer relative to the field of view coincides with a predetermined orientation. A second image of the wafer, having the predetermined position and predetermined orientation is then recorded and used for determining defects of the wafer. Such second images obtained from plural wafers, each positioned and oriented according to the predetermined position and orientation, can be compared with each other and analyzed in combination to determine defects of individual wafers which would not be determinable from the image of one single wafer alone. The second images used in such wafer-to-wafer comparison of plural wafers can be obtained under bright-field illumination and dark-field illumination.

Figure 2:
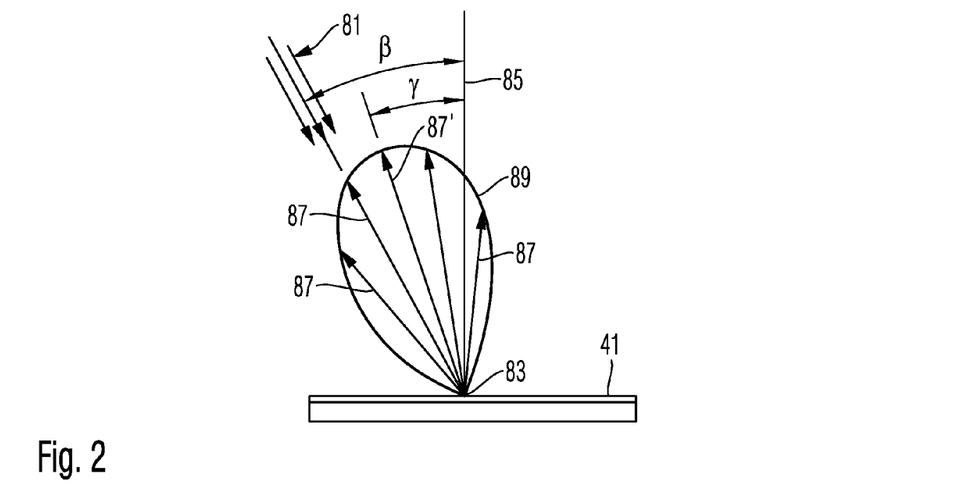
FIG. 2 is a schematic illustration of properties of a retroreflecting surface.

FIG. 2 illustrates a retroreflecting property of the surface portions 41. Reference numeral 81 in FIG. 2 designates a collimated beam of light incident on a location 83 on the surface of the surface portion 41. The beam of light 81 is incident on the surface portion 41 under an angle β relative to a direction 85 oriented orthogonal to the surface 41. Arrows 87 in FIG. 2 represent intensities of light reflected from the surface 41 at location 83. The light is reflected into different directions with different intensities. An envelope line 89 represents a distribution of the reflected light in dependence of the angle relative to the surface normal 85. A direction of maximum intensity of the reflected light is represented in FIG. 2 by an arrow 87'. The arrow 87' is oriented relative to the surface normal 85 under an angle γ which is smaller than the angle β but greater than 0. In particular, an angle between the direction of incidence and the orientation of the maximum intensity is smaller than 0.9 β. It is apparent that the angular distribution 89 of the reflected light intensities is different from an angular distribution of reflected intensities provided by a mirror or provided by a surface following Lambert's law. In FIG. 2 the angle γ is substantially smaller than the angle β for illustrative purposes. In practice, when suitable retroreflecting surfaces are used, it is possible that the angle γ is equal to or only slightly smaller than the angle β for values of β of 5°, 10° or even greater values of β. Also, the arrow 87' is located in the same quadrant or on the same side with respect to the surface normal 85 as the direction of the incident light. In other words, an angle |β−γ| between the direction of incidence of the light beam 81 and the direction of the maximum intensity 87' of the reflected light is smaller than the angle β between the direction of incidence of the light beam 81 and the surface normal 85 of the surface portion 41.

The retroreflective surface portions 41 used in the present example can be provided by various retroreflective materials. For example, retroreflective materials can be used which are supplied by the 3M™ company under the tradename Scotch-Light™.

Figure 3:
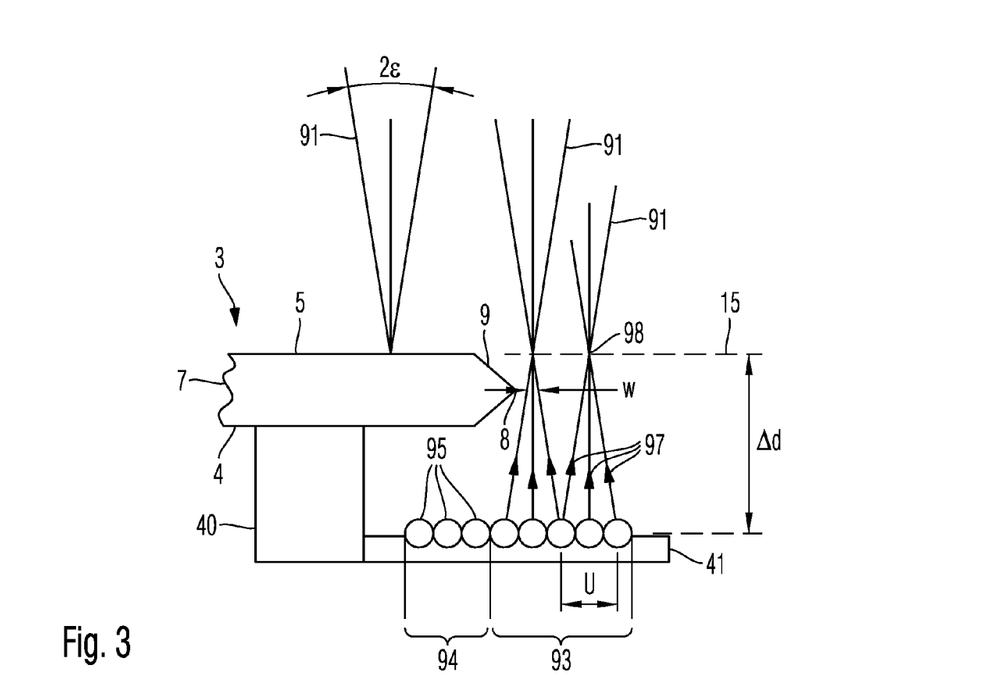
FIG. 3 is a schematic illustration of a detail of FIG. 1.

FIG. 3 illustrates a detail of the system shown in FIG. 1. Cones 91 in FIG. 3 represent illumination light beam bundles and imaging beam bundles focused on the object plane 15 at and originating from the object plane at exemplary locations 98, wherein an opening angle 2ε of the cones 91 correspond to two times a numerical aperture NA of the bright field illumination beam path 31 and the imaging beam path 13 on the side of the object plane 15. The light of the beam bundles 91 of the illumination beam path converges above the object plane 15 and diverges below the object plane 15. The retroreflecting surface portion 41 is, in the illustrated embodiment, attached to the back side 4 of the wafer 3 by an intermediate connection portion 40 and located at a distance Δd from the object plane 15 such that bright field illumination light is incident on a portion 93 of the surface portion 41 and such that the wafer 3 shadows a portion 94 of the retroreflecting surface portion 41 such that bright field illumination light is not incident on the portion 94. Reference numeral 95 indicates individual retroreflectors provided on the surface portion 41.

The individual retroreflectors can be formed by beads or prisms of a material having a high refractive index embedded in a reflecting material or by other configurations. FIG. 3 shows a low number of exemplary retroreflectors 95 for illustrative purposes. In practice, the number of retroreflectors per unit area can be high. For example, more than 10, more than 100, more than 1.000 or mare than 10.000 retroreflectors can be provided per cm² of the retroreflecting surface 41.

Due to the fact that the wafer 3 has a certain thickness and possibly due to other limitations of the wafer mount 45, it is not possible to position the retroreflecting surface portion 41 in the object plane 15 or immediately below the object plane, and the distance Δd has to be provided between the surface portion 41 and the object plane 15 to allow for the overlap between the wafer 3 and the retroreflecting surface portion 41 such that the wafer shadows the portion 94 of the retroreflecting surface portion 41 when seen from the camera 19. The shadow of the wafer 3 defined by the wafer edge 8 formed on the retroreflecting surface portion 41 is not sharply defined since the light cones 91 diverge below the object plane 15. However, the controller 55 is configured such that it detects the wafer edge and/or wafer notch based on an image analysis of the light reflected back from the surface 41. If the surface 41 was formed by a mirror material or a material which is described by Lambert's law, the detected light intensity would gradually rise from 0 to the maximum reflected intensity with increasing distance from the wafer edge. It is possible to determine a location of a wafer edge or notch based on such gradually increasing light intensity. However, such determination of the location would be inaccurate and significantly depend on the distance Δd and the model chosen to simulate the gradually increasing light intensity.

In the present example, retroreflective material is provided at the distance Δd from the object plane 15, and arrows 97 represent retroreflected light rays originating from two light cones 91 focused at two exemplary locations 98. It is apparent that the light is reflected back in itself such that the light reflected back and received and accepted by the objective lens 21 appears to substantially originate from the locations 98 on the object plane 15 even though the light originating from a location 98 was reflected back at the retroreflective surface 41 from plural retroreflectors extending over a distance u. It is apparent that an increase of light intensities from 0 to the maximum intensity as detected by the camera 19 at the wafer edge is spread over a relatively small distance allowing for a precise detection of the wafer edge via image analysis performed in the controller 55. The distance over which the intensity raises at the wafer edge can be slightly increased by the fact that the wafer edge 8 is at the end of a bevel 9 and located at a small distance from the object plane. This suggests that the distance over which the intensity rises is defined by a width w of the light cone 91 at a position of the wafer edge 8. This width w is considerably smaller than the width u at the retroreflective surface 41. By using the retroreflecting surface 41, it is possible to obtain satisfactory results from the image analysis even when the retroreflecting surface 41 is located at a considerable distance Δd from the object plane 15. For example, Δd can be greater than 2 mm, greater than 10 mm or even greater. Moreover, the retroreflecting surface 41 can be located outside of a depth of field of an imaging optics used for the imaging. The depth of field can be represented by the equation $\Delta f = 2\lambda/NA^2$, and Δd can be greater than Δf, greater than 5 times Δf, greater than 10 times Δf or even greater.

Figure 4:
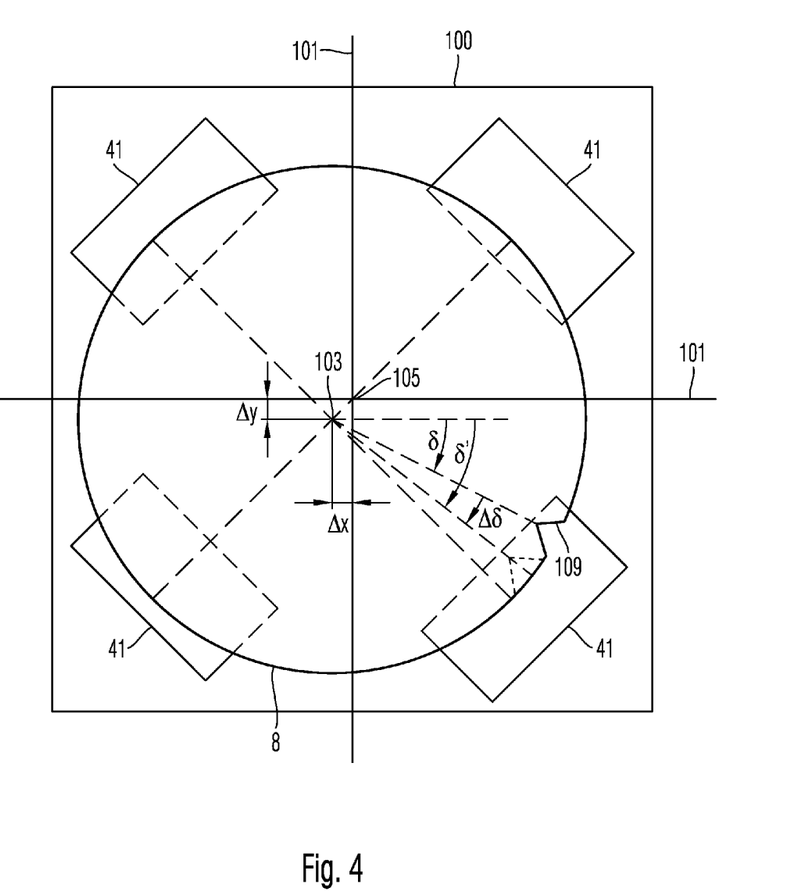
FIG. 4 is a schematic illustration of a further detail of the system shown in FIG. 1.

FIG. 4 is an illustration of an elevational view of the wafer 3 and retroreflective surface portions 41 which are positioned within a field of view 100 as seen from the camera 19. In this illustrated embodiment, the retroreflective surface portions 41 are attached to the wafer mount and not to the wafer. The principles illustrated in connection with this embodiment are, however, illustrative and also applicable to embodiments in which the retroreflective surface portions 41 are attached to the wafer. A position of the wafer edge 8 can be precisely determined in a coordinate system 101 of the system 1 by an analysis of images recorded by the camera 19. Based on the wafer edge, it is possible to determine a center 103 of the wafer which does not necessarily coincide with a center 105 of the coordinate system 101 and is spaced apart from the center 105 by a distance Δx in the horizontal direction and a distance Δy in the vertical direction. Moreover, one of the retroreflecting surface portions 41 is located on the stage 49 such that it coincides with an expected location of the wafer notch 109 when the wafer is positioned as expected on the wafer mount 45. It is apparent that also the notch portion of the wafer shadows a portion of the retroreflective portion 41 and that a position of the wafer notch 49 can be precisely determined from an analysis of an image recorded by the camera 19. The position of the wafer notch determines an orientation δ of the wafer relative to the coordinate system 101 which may deviate from a desired orientation δ' by a difference angle Δδ. Based on the determined deviations Δx, Δy and Δδ, the controller 55 may drive the actuators 53 and such that the center of the wafer coincides with the center of the coordinate system 101 and such that Δδ vanishes. After such displacement and rotation, the wafer is optimally oriented relative to the system 1 and the imaging beam path such that the camera 19 may record an image of the waver surface which allows a precised determination of coordinate of defects and deteriorations on the wafer in the coordinate system of the wafer itself.

A further embodiment of an object mount and stage which can be used in the system illustrated with reference to FIGS. 1 to 4 above will be illustrated with reference to FIGS. 5 to 9 below.

Figure 5:
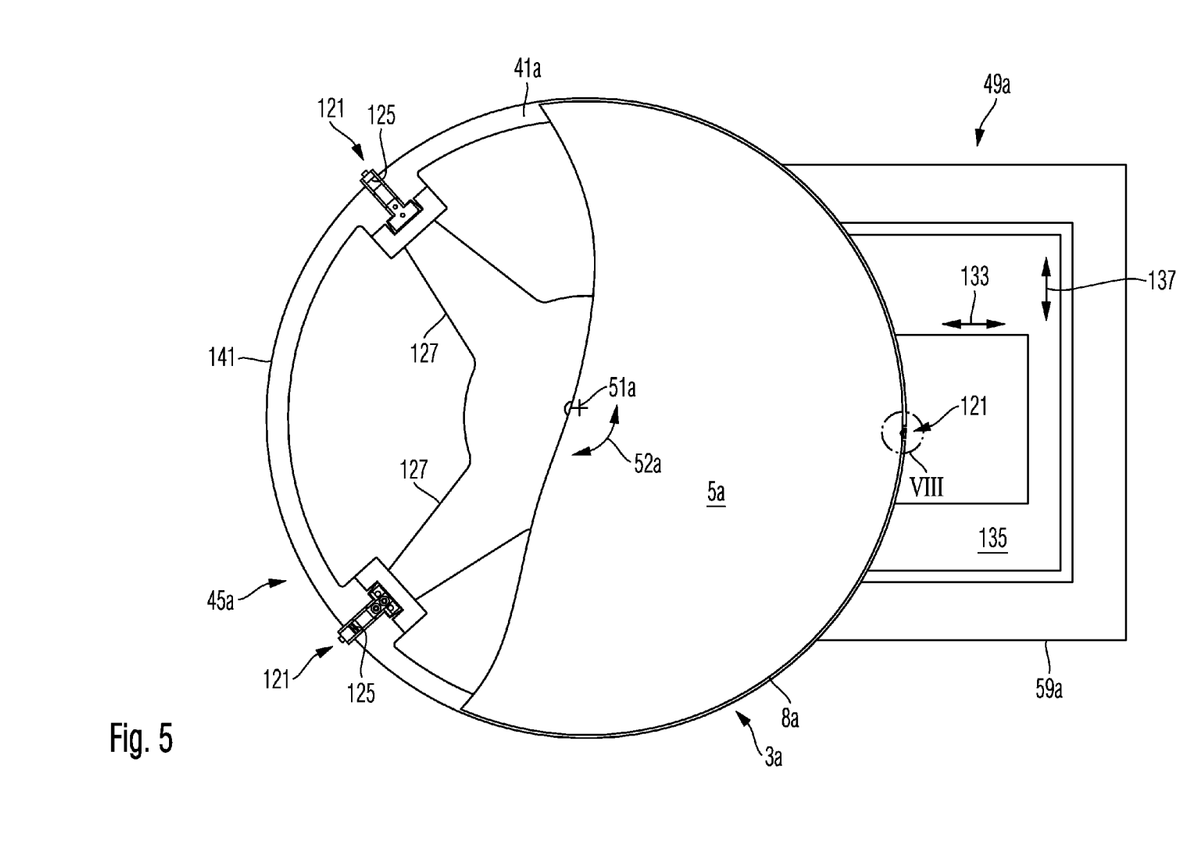
FIG. 5 is an elevational view of an embodiment of an object mount and a stage which can be used in the detection system shown in FIG. 1.
Figure 7:
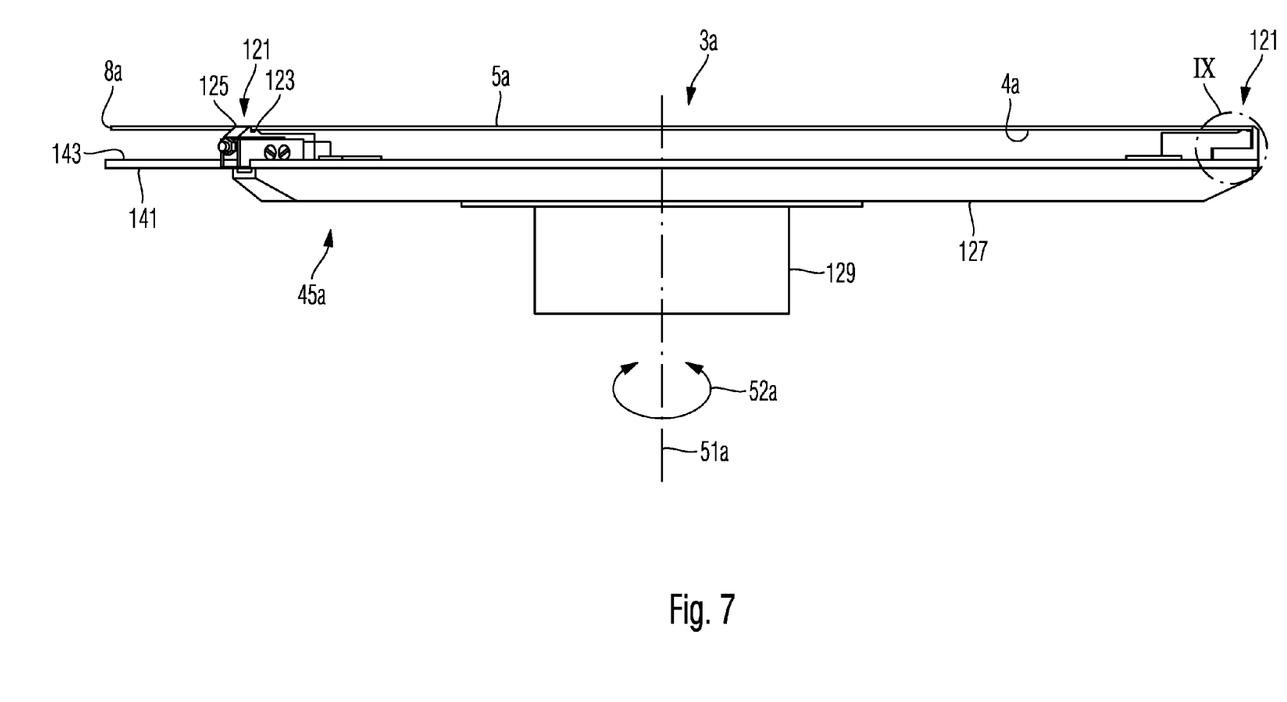
FIG. 7 is a side view of the object mount shown in FIG. 5.
Figure 8:
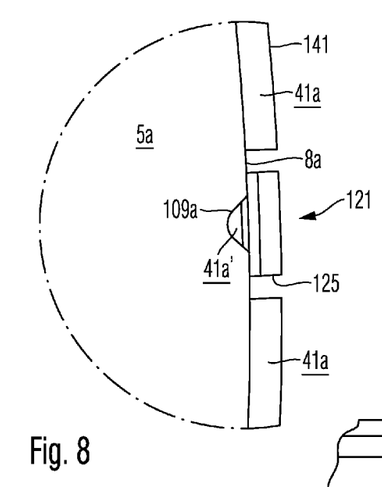
FIG. 8 is a detailed view of a portion VIII in FIG. 5.
Figure 9:
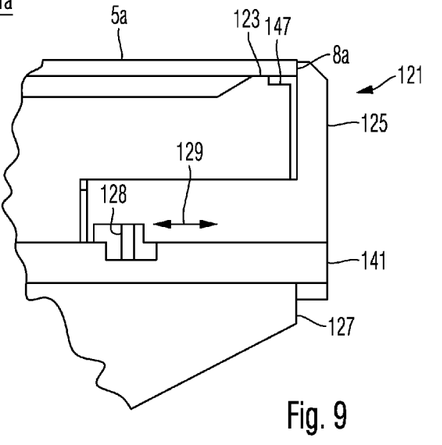
FIG. 9 is a detailed view of a portion IX in FIG. 7.

FIG. 5 is an elevational view of a 300 m wafer 3a mounted on a wafer mount 45a wherein a portion of the wafer 3a is broken away to show details of the wafer mount 45a. FIG. 7 is a side view of the wafer mount 45a, and FIGS. 8 and 9 show details VIII and IX of FIGS. 5 and 7, respectively.

The wafer 3a is attached to the wafer mount 45a by three attachment structures 121. The attachment structures 121 each comprise a nose portion 123 abutting on a back surface 4a of the wafer, and a lateral grip portion 125 abutting on the wafer edge 8a. In two of the attachment structures 121, the nose portion 123 and the grip portion 125 have a fixed relation to each other and can be integrally formed of one piece. One attachment structure 121 which is shown in FIG. 9 in detail has the attachment structure 121 configured such that the nose portion 123 is fixed relative to a support 127 carrying the three attachment structures 121 while the grip portion 125 can be displaced relative to the support 127 in a lateral direction as indicated by an arrow 129 shown in FIG. 9. The displacement of the grip portion 125 relative to the support 127 is controlled by an actuator 128 which can be operated to release the wafer and to grip the wafer 3a by applying a force to the wafer edge 8a.

The support 127 is carried by a bearing 129 received by a component 47a of a wafer stage 49a. The component 47a and bearing 129 include a motor, such as a piezoelectric motor, to rotate the support 127 and wafer 3a about an axis 51a relative to the component 47a, as indicated by an arrow 52a in FIGS. 5 and 7.

Figure 6:
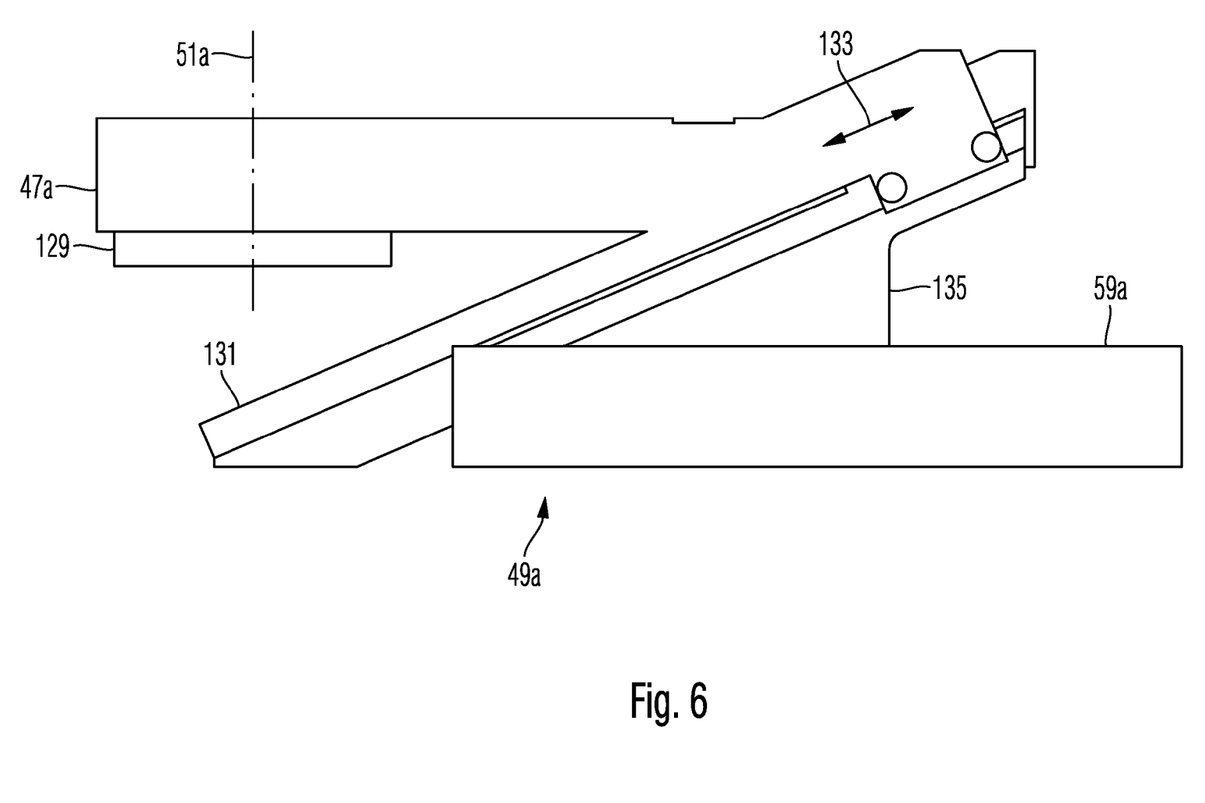
FIG. 6 is a side view of the stage shown in FIG. 5.

The component 47a is mounted on a carriage 131 allowing displacement of the component 47 relative to a base 59a of the stage 49a in an inclined direction as illustrated by an arrow 133 in FIG. 6. The displacement in direction 133 is controlled by a motor, such as a piezoelectric motor. The carriage 131 is mounted on a component 135 which can be displaced relative to the base 59a in a horizontal direction as indicated by an arrow 137 in FIG. 5. Again, the displacement in the direction 137 is controlled by a motor, such as a piezoelectric motor.

A movement of the component 47a relative to the carriage in the direction 133 does also result in a horizontal displacement of the wafer 3a relative to the base 59a. By controlling the respective motors for displacement in the directions 133 and 137, it is possible to achieve a controlled displacement of the wafer 3a relative to the base in two orthogonal horizontal directions, and the wafer 3a can also be rotated relative to the base 59 about the axis 51a.

The support 127 carries a ring 141 having a top surface 143 on which a retroreflective material is applied to provide a ring shaped retroreflective surface portion 41a. The retroreflective surface portion 41a is configured such that, when seen from above in the elevational view of FIG. 5, it extends beyond the wafer edge 8a. A camera onto which the wafer surface 5a and retroreflective surface portion 41a are imaged will then be able to precisely detect the wafer edge 8a relative to the detected image. Moreover, a notch 109a of the wafer 3a can be detected by the camera if the notch is positioned above the ring shaped surface portion 41a carried by the ring 141. Therefore, it is possible to determine an orientation of the wafer 3a relative to the camera by analysing the detected image as illustrated above.

The retroreflective surface portion 41a attached to the ring 141 does not extend completely around the periphery of the wafer 3a due to the presence of the three attachment structures 121. This has a consequence that the wafer notch 109a can not be detected based on light retroreflected from the retroreflective surface portions 41a carried by the ring 141, if the wafer notch happens to be positioned such that it is close to one of the attachment structures 121. To allow for detection of the wafer notch 109a also in situations where the wafer notch coincides with the attachment structures 121, a surface portion 147 close to the nose portion 123 of each attachment structure 121 carries retroreflective material to provide a retroreflective surface 41a'.

FIG. 8 illustrates a situation where the wafer 3a is oriented such that the wafer notch 109a coincides with one of the attachment structures 121. Light reflected back from the retroreflective surface portion 41a' and recorded by the camera allows determination of a position of the notch 109a within the detected image. The orientation of the wafer 3a within the image can be determined also in situations whether wafer notch 100a coincides with the wafer attachment structures 121, accordingly.

Figure 10:
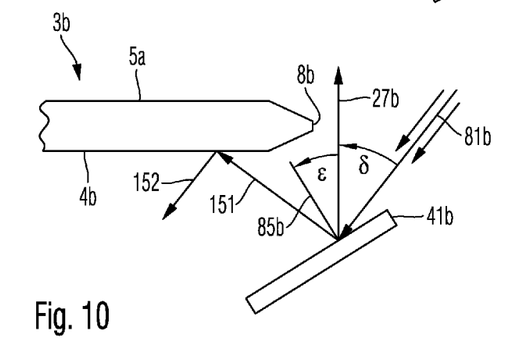
FIG. 10 is an illustration of a variation of the detail shown in FIG. 2.

FIG. 10 is a schematic illustration similar to FIG. 2, wherein a surface normal 85b of a retroreflective surface portion 41b is oriented under an angle c relative to a direction 27b of an imaging beam path. Due to the retroreflective property of the surface portion 41b, a significant portion of incident dark field illumination light 81b is retroreflected back along its direction of incidence. It is, however, possible that a portion of the incident light experiences diffuse scattering at the surface portion 41b. Arrow 151 in FIG. 10 illustrates an exemplary ray of light which is diffusely scattered at the surface portion 41b. This ray of light is incident on a back surface 4b of a wafer 3b and is absorbed at the back surface 4a. If a portion of that ray is not absorbed, as indicated by an exemplary ray 152, it will still not be detected by a camera imaging a wafer edge 8b and the surface portion 41b. By inclining the retroreflective surface portion 41b relative to the incident light 81b such that the angle c is greater than 10° or 20° or even greater than 30°, it is possible to reduce the amount of stray light received by the camera. Moreover, tilting of the retroreflective surface portion 41b relative to the incident dark-field illumination light reduces the amount of reduces the amount of dark-field illumination light to which the surface portion is exposed. For this purpose, an angle δ between the direction of incidence of the dark-field illumination light 81b and the surface normal 85b of the surface portion 41b can be greater than 50°, greater than 70° or even close to 90°.

A further example of a possibility to reduce an amount of stray light received by a camera in a dark field illumination mode is illustrated with reference to FIG. 1 below. Due to the retroreflective property of the retroreflective surface portion 41, a predominant amount of dark field illumination light incident on the surface portion 41 is retroreflected back towards the dark field illumination light source 73 as indicated by an arrow 159 in FIG. 1. A portion of the incident dark field illumination light can be still diffusely scattered at the surface portion 41. This portion of stray light could finally reach the camera 19, possibly after one or more reflections at other structures of the system 1. To further reduce the amount of stray light received by the camera 19, it is possible to configure the retroreflective material 41 such that it reflects back only light from within a narrow wavelength range, such as a wavelength range from 400 nm to 450 nm. Incident light of wavelengths outside of the narrow wavelength range is substantially absorbed by the retroreflective surface portion 49.

A blocking filter 157 is disposed in the imaging beam path 13 upstream of the camera 19. The blocking filter 157 is configured such that it blocks light from within the narrow wavelength range and allows light outside the wavelength range to traverse the filter 157. The camera 19 will not receive stray light generated by dark field illumination light incident on the retroreflective surface portions 41, accordingly.

The system 1 comprises an actuator 161 configured to displace the filter 157 from a position within the imaging beam path 13 to a position outside of the imaging beam path as indicated by an arrow 163 in FIG. 1. The filter 157 is moved to its position outside of the beam path, if the position of the wafer 3 is to be determined from an image recorded by the camera 19 under bright field illumination. The light retroreflected back from the retroreflective surface portions 41 within the narrow wavelength range can be received by the camera since the filter 157 is no longer disposed in the beam path upstream of the camera 19.

Figure 11:
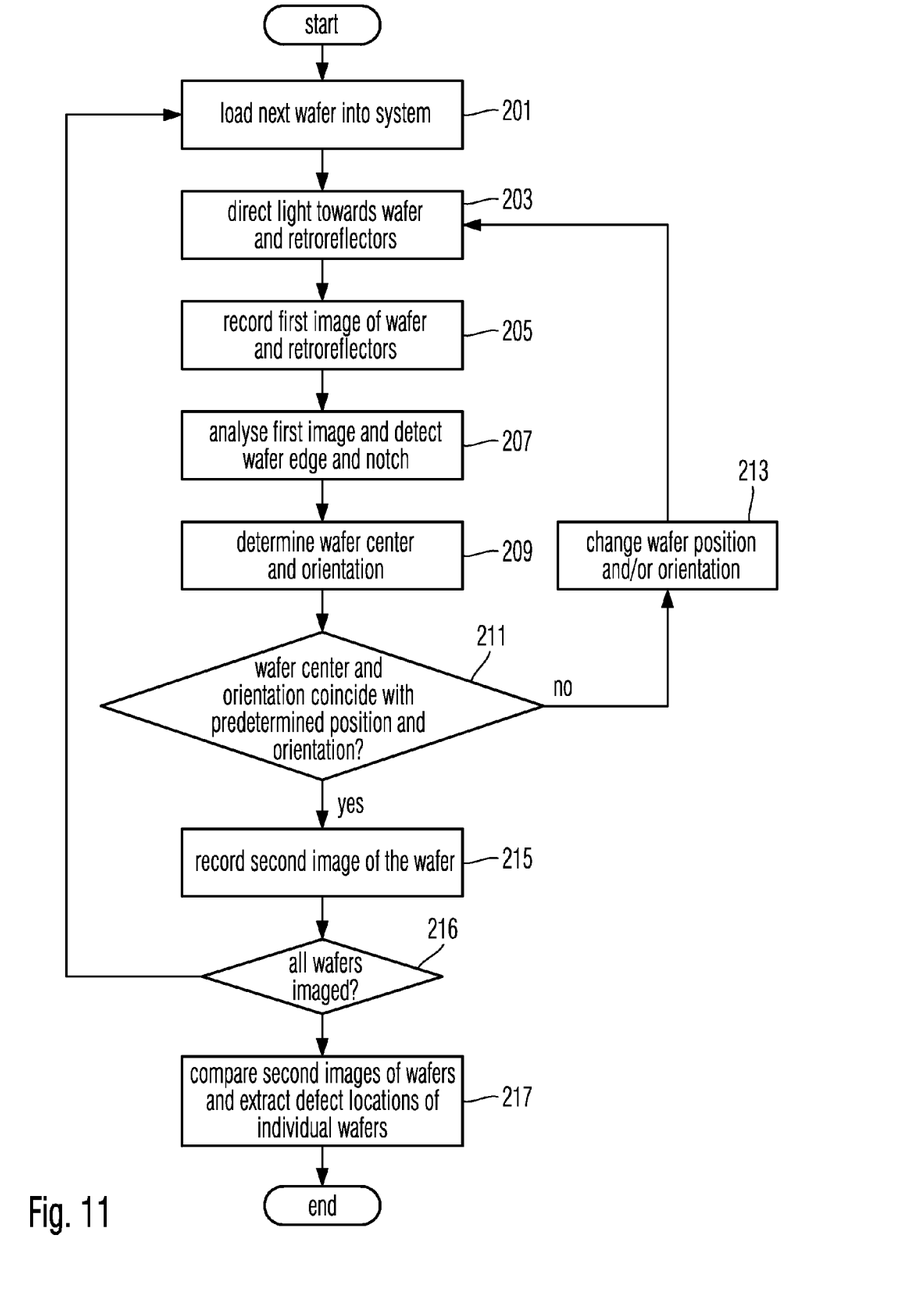
FIG. 11 is a flow-chart illustrating a positioning method.

FIG. 11 is a flow-chart illustrating a wafer inspection method. A first wafer of a set of wafers is loaded into the inspection system by placing the wafer on a wafer mount by a suitable wafer handler in a step 201. Light is directed towards the wafer and retroreflectors in a step 203. Light received from the wafer and the retroreflectors is recorded as a first image in a step 205. The recorded first image is analysed to detect a wafer edge and a wafer notch in a step 207. A center of the wafer and an orientation of the wafer is determined in a step 209. The determined wafer center and orientation is compared with a predetermined position and a predetermined orientation in a step 211. If the comparison reveals that the position of the wafer center and the orientation of the wafer do not coincide with the predetermined position and orientation, the position and orientation of the wafer is corrected via actuators in a step 213 and a processing according to steps 203, 205, 207, 209 and 211 is repeated. If the determination in step 211 reveals that the wafer center and orientation fulfil the requirement, a second image of the wafer is recorded in the step 215.

Thereafter, a next wafer of the set of wafers is loaded into the system in step 201, if a comparison 216 does not determine that all wafers of the set of wafers have been imaged. The next wafer is again positioned relative to the optics and a second image of the positioned wafer is recorded as illustrated above.

The set of second images of all wafers is analyzed in a step 217. Such analysis can be based on a common analysis of all second images and comprise a comparison of each individual image with one or more other second images to determine defect locations of the individual wafer. In particular, a reference wafer image can be computed from the plural second images by applying operations such as averaging to the images. The second images of the individual wafers can then be compared with the reference wafer image to determine defect locations of the individual wafer.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

The invention claimed is:

1. A semiconductor wafer inspection system comprising:
a light source;
a camera having a field of view;
an object mount configured to position a surface of a wafer at an object plane relative to the camera and within the field of view of the camera;
optics configured to provide an imaging beam path for imaging the object plane onto a light sensitive substrate of the camera, and to provide a bright-field illumination beam path from the light source to the object plane, wherein an angle at the object plane between a main axis of the imaging beam path and a main axis of the bright-field illumination beam path is smaller than 2°;
an actuator configured to displace the object mount in a direction parallel to the object plane or to rotate the object mount about an axis oriented transverse to the object plane; and
a surface portion carrying a multitude of retroreflectors disposed at a greater distance from the camera than the object plane and within the field of view of the camera;
wherein at least one of the following relation is fulfilled:

$$\Delta d > 0.1 * \lambda / NA^2 \text{ and } \Delta d > 2 \text{ mm wherein}$$

Δd is a difference between a distance of the surface portion from the camera and a distance of the object plane from the camera, wherein the distances are measured along the imaging beam path;
λ is a wavelength of light used for imaging; and
NA is a numerical aperture of the optics on the object side of the imaging beam path.

2. The semiconductor wafer inspection system according to claim 1, wherein the surface portion is attached to a component of the object mount which is displaced by the actuator together with the wafer.

3. The semiconductor wafer inspection system according to claim 2, wherein the object mount comprises a movable grip portion and a second actuator configured to push the movable grip portion against an edge of the wafer, and wherein the movable grip portion includes the at least one surface portion carrying the multitude of retroreflectors.

4. The semiconductor wafer inspection system according to claim 1, wherein the optics is configured such that an orientation of chief rays of the bright-field illumination beam path varies across the field of view by less than 5° and such that an orientation of chief rays of the imaging beam path varies across the object field by less than 5.

5. The semiconductor wafer inspection system according to claim 1, wherein the optics are configured such that a numerical aperture of the imaging beam path on a side of the object plane is less than 0.1, and such that a numerical aperture of the bright-field illumination beam path on a side of the object plane is less than 0.1.

6. The semiconductor wafer inspection system according to claim 1, wherein a surface normal of the surface portion is oriented under an angle of more than 10° relative to the main axis of the imaging beam path.

7. The semiconductor wafer inspection system according to claim 1, wherein the optics comprises at least one lens traversed by the imaging beam path and an illumination beam path.

8. The semiconductor wafer inspection system according to claim 1, wherein the optics is further configured to provide a dark-field illumination beam path from a light source to the object plane, wherein an angle at the object plane between a main axis of the imaging beam path and a main axis of the dark-field illumination beam path is greater than 10°.

9. The semiconductor wafer inspection system according to claim 8, wherein an angle between a direction of incidence of the dark-field illumination beam path on the surface portion and a surface normal of the surface portion is greater than 50°.

10. The semiconductor wafer inspection system according to claim 1, further comprising a controller connected to the camera and to the actuator, wherein the controller is configured to receive an image from the camera and to control the actuator for displacing the object mount based on an analysis of the received image.

11. The semiconductor wafer inspection system according to claim 1, wherein the multitude of retroreflectors are embedded in a coating of the surface portion and wherein a density of the multitude of retroreflectors in the surface portion is greater than 10/cm².

12. The semiconductor wafer inspection system according to claim 1, further comprising a blocking filter which can be selectively disposed inside and outside of a beam path between the surface portion and the camera, wherein the blocking filter is configured to block light from within a limited wavelength range while light with wavelengths outside of the limited wavelength range is substantially transmitted by the blocking filter, and wherein the surface portion is configured such that light from within the limited wavelength range is retroreflected while light with wavelengths outside the limited wavelength range is substantially absorbed.

13. A semiconductor wafer inspection method comprising:
loading a semiconductor wafer into a semiconductor wafer inspection system such that the semiconductor wafer and a multitude of retroreflectors on a surface portion are disposed in a field of view of an imaging system such that the semiconductor wafer shadows a portion of the multitude of retroreflectors and a surface of a wafer is positioned at an object plane relative to the imaging system and the imaging system comprises a light source, a camera and optics configured to provide an imaging beam path for imaging the object plane onto a light sensitive substrate of the camera, and to provide a bright-field illumination beam path from the light source to the object plane;
recording an image of the semiconductor wafer and the multitude of retroreflectors in the field of view;
analyzing the recorded image;
adjusting a position of the semiconductor wafer relative to the field of view by displacing the semiconductor wafer in a direction transverse to a direction of the bright-field illumination light path incident on the semiconductor wafer based on the analysis of the recorded image or rotating the semiconductor wafer about an axis oriented transverse to a surface of the semiconductor wafer based on the analysis of the recorded image;
wherein at least one of the following relation is fulfilled:

$$\Delta d > 0.1 * \lambda/NA^2 \text{ and } \Delta d > 2 \text{ mm wherein}$$

Δd is a difference between a distance of the surface portion from the camera and a distance of the object plane from the camera, wherein the distances are measured along the imaging beam path;
λ is a wavelength of light used for imaging; and
NA is a numerical aperture of the optics on the object side of the imaging beam path.

14. The method according to claim 13, further comprising directing bright field illumination light onto the object and wherein the recorded image is a bright field image of the object.

15. The method according to claim 13, further comprising directing dark field illumination light onto the object and recording a dark field image of the object.

16. The method according to claim 13, further comprising coupling the multitude of retroreflectors to the semiconductor wafer such that the adjusting the position of the semiconductor wafer includes a displacing of the multitude of retroreflectors together with the semiconductor wafer.

17. The method according to claim 13, wherein the analyzing of the recorded image comprises identifying an edge of the semiconductor wafer in the recorded image and determining a position of a center of the semiconductor wafer within the field of view based on the identified edge; and identifying a notch of the semiconductor wafer in the recorded image and determining an orientation of the semiconductor wafer within the field of view based on the identified notch.

18. The method according to claim 17, wherein the adjusting the position of the semiconductor wafer comprises positioning the semiconductor wafer such that the center of the wafer coincides with a predetermined position and such that the orientation of the wafer coincides with a predetermined orientation.

19. The method according to claim 18, further comprising loading, one after the other, a plurality of semiconductor wafers into the semiconductor wafer inspection system, wherein the position of each semiconductor wafer is adjusted such that the center of the semiconductor wafer coincides with the predetermined position and such that the orientation of the semiconductor wafer coincides with the predetermined orientation, and wherein the method further comprises recording a second image of each semiconductor wafer subsequent to the adjusting of the position of the semiconductor wafer, and determining a presence of defects on a given semiconductor wafer based on a comparison of the recorded second image of the given semiconductor wafer with recorded second images of other semiconductor wafers.

20. The method according to claim 19, wherein the recording of second images comprises illuminating the semiconductor wafers with one of bright-field illumination light and dark-field illumination light.

21. A semiconductor wafer inspection system comprising:
a light source;
a camera having a field of view;
an object mount configured to position a surface of a wafer at an object plane relative to the camera and within the field of view of the camera;
optics configured to provide an imaging beam path for imaging the object plane onto a light sensitive substrate of the camera, and to provide a bright-field illumination beam path from the light source to the object plane, wherein an angle at the object plane between a main axis of the imaging beam path and a main axis of the bright-field illumination beam path is smaller than 2°;
an actuator configured to displace the object mount in a direction parallel to the object plane or to rotate the object mount about an axis oriented transverse to the object plane; and
a surface portion carrying a multitude of retroreflectors disposed at a greater distance from the camera than the object plane and within the field of view of the camera;
wherein the surface portion is configured such that the following relation is fulfilled:

$$|\beta - \gamma| < 0.9 * \beta, \text{ wherein}$$

β is an angle between a direction of incidence of a collimated beam of light on the surface portion and a surface normal of the surface portion, and γ is an angle between an orientation of a maximum of an angular intensity distribution of light reflected from the surface portion and the surface normal of the surface portion.

22. A semiconductor wafer inspection method comprising:
loading a semiconductor wafer into a semiconductor wafer inspection system such that the semiconductor wafer and a multitude of retroreflectors on a surface portion are disposed in a field of view of an imaging system such that the semiconductor wafer shadows a portion of the multitude of retroreflectors;
recording an image of the semiconductor wafer and the multitude of retroreflectors in the field of view;
analyzing the recorded image;
adjusting a position of the semiconductor wafer relative to the field of view by displacing the semiconductor wafer in a direction transverse to a direction of a bright-field illumination light path incident on the semiconductor wafer based on the analysis of the recorded image or rotating the semiconductor wafer about an axis oriented transverse to a surface of the semiconductor wafer based on the analysis of the recorded image;

wherein the surface portion is configured such that the following relation is fulfilled:

$|\beta-\gamma|<0.9*\beta$, wherein

β is an angle between a direction of incidence of a collimated beam of light from the semiconductor wafer inspection system on the surface portion and a surface normal of the surface portion, and γ is an angle between an orientation of a maximum of an angular intensity distribution of light reflected from the surface portion and the surface normal of the surface portion;

Δd is a difference between a distance of the surface portion from the camera and a distance of the object plane from the camera, wherein the distances are measured along the imaging beam path;

λ is a wavelength of light used for imaging; and

NA is a numerical aperture of the optics on the object side of the imaging beam path.

* * * * *